United States Patent [19]
Elliott et al.

[11] Patent Number: 5,359,103
[45] Date of Patent: Oct. 25, 1994

[54] MANUFACTURE OF FERROUS PICRATE

[75] Inventors: Alan F. Elliott, South Melbourne; Glen B. Deacon, Clayton; William R. Jackson, Glen Waverley, all of Australia

[73] Assignee: FPC Australia, Inc., Australia

[21] Appl. No.: 888,490

[22] Filed: May 27, 1992

[51] Int. Cl.$^5$ .............................. C07F 15/02
[52] U.S. Cl. .................................... 556/150
[58] Field of Search ............. 149/23; 556/138, 146, 556/190

[56] References Cited

U.S. PATENT DOCUMENTS

| | | | |
|---|---|---|---|
| 2,202,647 | 5/1940 | Brun | 556/150 |
| 3,282,858 | 11/1966 | Simmons et al. | 252/428 |
| 4,073,626 | 2/1978 | Simmons | 44/57 |
| 4,099,930 | 7/1978 | Webb | 44/56 |
| 4,129,421 | 12/1978 | Webb | 44/56 |
| 4,145,190 | 3/1979 | Webb | 44/56 |
| 4,265,639 | 5/1981 | Scholtz | 44/57 |
| 4,424,063 | 1/1984 | Hart | 44/56 |
| 4,506,539 | 5/1950 | Boardman | 44/68 |
| 5,087,268 | 2/1992 | Parish | 556/150 |

FOREIGN PATENT DOCUMENTS

| | | |
|---|---|---|
| 621243 | 6/1991 | Australia . |
| 5790490 | 9/1991 | Australia . |

OTHER PUBLICATIONS

Feijer & Feiser, *Advanced Organic Chemistry*, p. 685, Reinhold Publ. Corp. (1961) New York.
Bailar et al., *Comprehensive Inorganic Chemistry*, 3, pp. 990, 996, 1010, Pergamon Press (1973) Oxford.

*Primary Examiner*—Edward A. Miller
*Attorney, Agent, or Firm*—Frank P. Presta

[57] ABSTRACT

A process for preparing ferrous picrate comprising reacting picric acid in solution in a straight- or a branched-chain aliphatic alcohol with an iron carbonyl at a temperature between 10° C. and 120° C.

17 Claims, No Drawings

MANUFACTURE OF FERROUS PICRATE

This invention relates to the manufacture of ferrous picrate. For some purposes, for example as an additive for carbonaceous fuel it is, highly desirable that ferrous picrate be substantially free from ferric compounds and other undesirable impurities. It has proved difficult to produce ferrous picrate suitable for use as a fuel additive by a commercially acceptable method. All processes of purification described in the patent literature involve several steps, resulting in low yields and rendering the product expensive. In addition, as ferrous picrate and picric acid in the solid state may be explosive, the necessary precautions in the manufacture and handling of the solid material further increase the cost.

It is the principal object of the present invention to provide a process for producing ferrous picrate whereby the number of process steps is reduced, and the presence of ferric compounds and other impurities is minimised.

It is a further object of the present invention to provide a process for preparing ferrous picrate in a solution which is safe to handle and is suitable for incorporation in an additive for carbonaceous fuels.

In order to achieve the above stated objects, the present invention provides a process for preparing ferrous picrate comprising reacting picric acid in an aromatic hydrocarbon solvent or in a straight- or branched-chain aliphatic alcohol, or in a mixture of both, with an iron carbonyl at a temperature between 10° C. and 120° C.

The reaction is preferably carried out under a continuously maintained inert atmosphere, e.g. nitrogen.

The preferred temperature range for the reaction is between 20° C. and 80° C., most preferably between 40° C. and 70° C.

The preferred aromatic hydrocarbon solvents are alkylbenzenes, e.g. toluene or xylene and the preferred alcohols are $C_3$–$C_8$ straight- or branched-chain aliphatic alcohols, e.g. isopropyl alcohol, n.butanol or iso-octanol.

The preferred iron carbonyl is iron pentacarbonyl.

The ferrous picrate solution resulting from the process may be added directly to a further quantity of an aromatic solvent, e.g. toluene, xylene, or mixtures thereof, or a straight- or branched-chain aliphatic alcohol, or mixtures of both, to produce a fuel additive.

Practical examples of processes according to the present invention will now be described.

EXAMPLE 1

2.5 g of dry picric acid was added to 250 mL isopropanol in a reaction flask fitted with a reflux condenser, flushed with nitrogen and vented to a fume hood. The temperature of the mixture was raised to 45° C. in a thermostatically controlled bath. 0.9 mL of iron pentacarbonyl was then added to the mixture, and allowed to react until the maximum level of ferrous picrate was reached, i.e. about 18 hours. Nitrogen was passed continuously through the flask during this time. The reaction liquid became dark green and all the picric acid was in solution. The ferrous iron content was found to be 1200 mg/n.

EXAMPLE 2

Picric acid (4 g dry weight) was added in the form of an aqueous slurry to 200 mL of xylene in a separating flask. The mixture was stirred until the picric acid had dissolved and was then allowed to stand for several hours by which time the aqueous phase had settled to the bottom of the flask. The aqueous phase was then drained off. Dried silica gel (about 5 g) was then added to the liquid remaining in the separating flask. The mixture was stirred at intervals over about 24 hours. The liquid was then separated from the silica gel by filtration and transferred to a reaction flask fitted with a reflux condenser. To the liquid was then added 100 mL of n.butanol followed by 0.5 mL of iron pentacarbonyl. Nitrogen was passed continuously through the flask and the temperature was adjusted to 60° C. A dark green solution of ferrous picrate was obtained.

EXAMPLE 3

Picric acid (2.5 dry weight) was added in the form of an aqueous slurry to 150 mL of toluene. The water was removed by azeotropic distillation before adding 100 mL of n.butanol and the iron pentacarbonyl as described in Example 1. Nitrogen was passed continuously through the flask during this time. A dark green solution of ferrous picrate was obtained.

EXAMPLE 4

The procedure described in Example 1 was repeated, except that picric acid (5 g dry weight) was added in the form of an aqueous slurry to 175 mL of xylene. After azeotroping off the water, 75 mL of iso-octanol was added, followed by the iron pentacarbonyl at 45° C. A dark green solution of ferrous picrate was obtained.

EXAMPLE 5

Picric acid (4 g dry weight) was added in the form of an aqueous slurry to 300 mL of xylene. After azeotroping off the water and allowing to cool to about 60° C., 200 mL of n.butanol and 0.5 mL of iron pentacarbonyl were added. The mixture was held at about 60° C. Nitrogen was passed continuously through the flask for several hours until the reaction was complete. A dark green solution of ferrous picrate resulted which on analysis was found to contain 400 mg/L of ferrous iron. Xylene (1.5 L) was added and mixed to produce an additive of the following composition for addition to diesel fuel:

Ferrous picrate: 1.8 g
Picric acid: 2.00 g
n.Butanol: 200 mL
Xylene: 1800 mL

We claim:

1. A process for preparing ferrous picrate comprising reacting picric acid in solution in a straight- or branched-chain aliphatic alcohol with an iron carbonyl at a temperature between 10° C. and 120° C.

2. A process according to claim 1, wherein the reaction is conducted under a continuously maintained inert atmosphere.

3. A process according to claim 2, wherein the inert atmosphere is an atmosphere of nitrogen.

4. A process according to claim 2, wherein the alcohol is a $C_3$–$C_8$ straight- or branched-chain aliphatic alcohol.

5. A process for preparing ferrous picrate comprising reacting picric acid in solution in a straight- or branched-chain aliphatic alcohol with an iron carbonyl at a temperature between 40° C. and 70° C.

6. A process according to claim 5, wherein the reaction is conducted under a continuously maintained inert atmosphere.

7. A process according to claim 6, wherein the inert atmosphere is an atmosphere of nitrogen.

8. A process according to claim 6, wherein the alcohol is a $C_3$–$C_8$ straight- or branched-chain aliphatic alcohol.

9. A process for preparing ferrous picrate comprising reacting picric acid in solution in a straight- or branched-chain aliphatic alcohol with iron pentacarbonyl at a temperature between 10° C. and 120° C.

10. A process according to claim 9, wherein the reaction is conducted under a continuously maintained inert atmosphere.

11. A process according to claim 10, wherein the atmosphere is an atmosphere of nitrogen.

12. A process according to claim 10, wherein the alcohol is a $C_3$–$C_8$ straight- or branched-chain aliphatic alcohol.

13. A process for preparing ferrous picrate comprising reacting picric acid in solution in a straight- or branched-chain aliphatic alcohol with iron pentacarbonyl at a temperature between 40° C. and 70° C.

14. A process according to claim 13, wherein the reaction is conducted under a continuously maintained inert atmosphere.

15. A process according to claim 14, wherein the atmosphere is an atmosphere of nitrogen.

16. A process according to claim 14, wherein the alcohol is a $C_3$–$C_8$ straight- or branched-chain aliphatic alcohol.

17. A process for preparing ferrous picrate comprising reacting picric acid in solution in an alcohol selected from the group consisting of isopropanol, n.butanol and iso-octanol with iron pentacarbonyl under a continuously maintained atmosphere of nitrogen at a temperature between 40° C. and 60° C.

* * * * *